United States Patent
Jhung et al.

(10) Patent No.: US 6,194,607 B1
(45) Date of Patent: Feb. 27, 2001

(54) METHOD OF PRODUCING AROMATIC CARBOXYLIC ACIDS BY OXIDIZING ALKYL AROMATIC HYDROCARBONS OR PARTIALLY OXIDIZED INTERMEDIATES THEREOF

(75) Inventors: Sung-Hwa Jhung; Youn-Seok Park; Ki-Hwa Lee, all of Taejeon-shi (KR); Jin Sun Yoo, Flossmoor, IL (US); Jong-Hyun Chae, Taejeon-shi (KR)

(73) Assignee: Samsung General Chemicals Co., Ltd., Seosan (KR)

( * ) Notice: Subject to any disclaimer, the term of this patent is extended or adjusted under 35 U.S.C. 154(b) by 0 days.

(21) Appl. No.: 09/453,537

(22) Filed: Dec. 3, 1999

(30) Foreign Application Priority Data

Dec. 22, 1998 (JP) .................................. 98-57386
Dec. 22, 1998 (JP) .................................. 98-57388

(51) Int. Cl.$^7$ .................................................. G07C 51/16
(52) U.S. Cl. .......................................... 562/412; 562/413
(58) Field of Search ..................................... 562/412, 413

(56) References Cited

U.S. PATENT DOCUMENTS

| | | |
|---|---|---|
| 2,833,816 | 5/1958 | Saffer et al. . |
| 3,584,039 | 6/1971 | Meyer . |
| 5,112,992 | 5/1992 | Belmonte et al. . |
| 5,183,933 | 2/1993 | Harper et al. . |
| 5,324,702 | 6/1994 | Yoo et al. . |
| 5,359,133 | 10/1994 | Nazimok et al. . |
| 5,371,283 | 12/1994 | Kingsley et al. . |
| 5,453,538 | 9/1995 | Broeker et al. . |
| 5,523,474 | 6/1996 | Kingsley et al. . |
| 5,596,129 | 1/1997 | Murashige et al. . |
| 5,693,856 | 12/1997 | Ramachandran et al. . |
| 5,696,285 | 12/1997 | Roby . |

FOREIGN PATENT DOCUMENTS

WO 96/41791   12/1996   (WO) .

OTHER PUBLICATIONS

J. Yoo, "Selective Gas–Phase Oxidation at Oxide Nanoparticles on Microporous Materials, " Catalysis Today, vol. 41 (1998), pp. 409–432.

J. Yoo, "Gas Phase Oxygen Oxidation of Alkylaromatics over CVD Fe/Mo/Borosilicate Molecular Sieve, Fe/Mo/DBH. VII. Oxidative Dehydrogenation of Alkylaromatics," Applied Catalysis A: General, vol. 142 (1996), pp. 19–29.

J. Yoo, "The CVD Fe/Mo/DBH (Deboronated Borosilicate Molecular Sieve) –Catalyzed Oxidation Reactions," Applied Catalysis A: General, vol. 143 (1996), pp. 29–51.

J. Yoo, "Gas–Phase Oxygen Oxidations of Alkylaromatics over CVD Fe/Mo/Borosilicate Molecular Sieve. VI. Effects of *para*–Substituents in Toluene Derivatives ," Allied Catalysis A: General, vol. 135 (1996), pp. 261–271.

J. Yoo, et al., "Gas–Phase Oxygen Oxidations of Alkylaromatics over CVD Fe/Mo/Borosilicate Molecular Sieve. II. The Role of Carbon Dioxide as a Co–Oxidant," Applied Catalysis A: General, vol. 106 (1993), pp. 259–273.

G. Zajac, et al., "Characterization and Oxidation Catalysis of Alkylaromatics over CVD Fe/Mo/Borosilicate Molecular Sieve: Fe/Mo/DBH," Journal of Catalysis, vol. 151, No. 2, Feb. 1995, pp. 338–348.

W. Partenheimer, "Methodology and Scope of Metal/bromide Autoxidation of Hydrocarbons, " J. Chem Soc. Chem. Commun., vol. 23 (1995), vol. 23 pp. 69–158.

M. Aresta, et al., "Carbon Dioxide as Modulator of the Oxidative Properties of Dioxide in the Presence of Transition Metal System," J. Chem. Soc. Chem. Commun., 1992, pp. 315–317.

*Primary Examiner*—Paul J. Killos
(74) *Attorney, Agent, or Firm*—Fitzpatrick, Cella, Harper & Scinto

(57) ABSTRACT

An improved production method of aromatic carboxylic acid products of significantly improved yield and quality by oxidizing alkyl aromatic substrates or their partially oxidized intermediates in a conventional MC-type catalyst system modified to contain additional components such as alkali metal or alkaline earth metal in an acetic acid medium in a feed gas containing oxygen and optionally carbon dioxide. Since carbon dioxide functioned as a co-oxidant along with oxygen in the oxidation reaction, the oxidation reaction proceeds more selectively to produce the carboxylic acid product much faster under milder reaction conditions over the conventional MC-type oxidation. In particular, the oxidation of para-xylene carried out by the novel present method enabled production of terephthalic acid of higher yield and enhanced quality, which were improved far more than the extent that generally could be expected by current PTA producers. The present invention also provides an effective purification process to produce highly pure terephthalic acid or isophthalic acid by the oxidation of impurities such as 4-carboxybenzaldehyde and para-toluic acid or 3-carboxybenzaldehyde and meta-toluic acid contaminated in crude terephthalic acid and isophthalic acid product, respectively.

35 Claims, No Drawings

METHOD OF PRODUCING AROMATIC CARBOXYLIC ACIDS BY OXIDIZING ALKYL AROMATIC HYDROCARBONS OR PARTIALLY OXIDIZED INTERMEDIATES THEREOF

BACKGROUND OF THE INVENTION

1. Field of the Invention

The present invention discloses an improved process for oxidizing alkyl aromatic hydrocarbons and/or their partially oxidized intermediates to produce aromatic carboxylic acids. The process involves the liquid phase oxidation in the presence of a catalyst of cobalt-manganese-bromine and alkali metal or alkaline earth metal, in an aliphatic carboxylic acid having 1~6 carbon atoms such as acetic acid as a solvent with a feed gas containing oxygen either with or without carbon dioxide. In particular, one or more than one type of alkali metal or alkaline earth metal components are preferably added to the catalyst system, and furthermore, an additional transition metal or lanthanide series metal is introduced to the catalyst system, cobalt-manganese-bromine, when it is deemed necessary.

The rate of the oxidation reaction of an alkyl aromatic substrate was remarkably increased in the present process over the conventional MC-type process (i.e., a liquid phase oxidation reaction using a cobalt-manganese-bromine catalyst). The yield and quality of the carboxylic acid product were also significantly improved by the present process. Thus, terephthalic acid of improved yield and purity is produced by carrying out the oxidation of para-xylene in the presence of a catalyst containing the additional components such as potassium and/or transition metal in the co-presence of carbon dioxide with oxygen, at relatively mild reaction conditions.

With the present invention, highly pure terephthalic acid or isophthalic acid can be produced by oxidizing impurities such as 4-carboxybenzaldehyde, para-toluic acid, 3-carboxybenzaldehyde, and meta-toluic acid contaminated in crude terephthalic acid and crude isophthalic acid, respectively.

2. Description of the Related Art

As discussed below, methods of manufacturing aromatic carboxylic acids are well known and are widely used commercially. For example, a method of manufacturing of aromatic carboxylic acids such as terephthalic acid (TPA), isophthalic acid (IPA), phthalic acid, phthalic anhydride, naphthalene dicarboxylic acid, trimellitic acid, trimellitic anhydride, trimesic acid, pyromellitic dianhydride, 4,4'-biphenyldicarboxylic acid and benzoic acid by oxidizing alkylaromatic compounds or the oxidized intermediates thereof, in the presence of cobalt-manganese-bromine, from such alkylaromatic compounds as para-xylene, para-tolualdehyde, para-toluic acid, 4-carboxybenzaldehyde (4-CBA), meta-xylene, meta-tolualdehyde, meta-toluic acid, 3-carboxybenzaldehyde, ortho-xylene, dimethylnaphthalene, pseudocumene (1,2,4-trimethylbenzene), mesitylene (1,3,5-trimethylbenzene), durene (1,2,4,5-tetramethylbenzene), pentamethylbenzene, hexamethylbenzene, 4,4'-dimethylbiphenyl and toluene is well known (for example, U.S. Pat. Nos. 2,833,816 and 5,183,933). Such aromatic carboxylic acids are used as raw materials for manufacturing polyester after appropriate purification such as hydrogenation, etc. (U.S. Pat. No. 3,584,039). Also, polyester is widely used as a synthetic fiber, film, etc.

There were continuous endeavors to develop a catalyst system with high efficiency and enhanced reactivity to manufacture aromatic carboxylic acids. The newly developed technologies, however, were not practical due to the increase of side reactions, price of catalyst, difficulty of operation, and precipitation of catalyst, etc.

Improvements of the efficiency of the reaction and the catalyst in the manufacturing of aromatic carboxylic acids are very significant because they may improve productivity, quality and cost competitiveness due to the reduction in the reaction time and side reactions. In other words, it is highly desirable to develop a technology to increase the efficiency of the oxidation reaction of alkyl aromatic compounds and the oxidized intermediates thereof by means of an improvement in the catalyst system or other reaction processes.

There were many attempts to increase the efficiency by adding a third metal catalyst to the cobalt-manganese-bromine catalyst system which is the basic catalyst system, to enhance the catalyst efficiency during the manufacturing of aromatic carboxylic acids. The added metals were mainly transition metals, and by adding, for example, hafnium, zirconium, molybdenum, etc., the reactivity therein was increased (U.S. Pat. No. 5,112,992). Further, as an example of an attempt to add an alkali metal component, a catalyst system was used, in which alkali metal components such as lithium, sodium and potassium were added to the cobalt-manganese-nickel-bromine catalyst system, in the presence of two or three types of bromine compounds. There, the method involved manufacturing of terephthalic acid of a monomer grade by a two-step process of oxidation and re-crystallization (WO96/41791). In that method, there is a disadvantage in that the catalyst system is very complicated, since nickel must be added to cobalt-manganese-bromine for the catalyst system and since more than two types of bromine compounds are necessary (both compounds having an ionic bond and those having a covalent bond are needed).

The newly developed technologies, however, were not practical due to the increase of the side reactions, price of catalyst, difficulty of operation, and precipitation of catalyst, etc. even though there were many attempts to develop a catalyst system for aromatic carboxylic acids with high efficiency and enhanced reactivity.

On the other hand, an oxygen containing gas such as air was mainly used as an oxidant during the manufacturing of aromatic carboxylic acids. Carbon dioxide was not used as an oxidant due to its chemical stability. Yet, in the research for improving the process efficiency, there was a case in which chemically stable carbon dioxide, recycled from the reaction vent gas, was injected to the reactor to increase the stability in the process by mitigating the problematic possibilities of explosion due to oxygen when using pure oxygen or gas containing pure oxygen or oxygen enriched gas as an oxidant (U.S. Pat. No. 5,693,856). Nevertheless, the case is not known in which carbon dioxide was added to improve the reaction efficiency.

In summary, the basic oxidation technologies for aromatic carboxylic acids manufacture, especially for TPA manufacture, have been extensively developed. The basic process technology is now approaching a point of diminishing returns, and further major breakthroughs i.e., new catalyst systems, raw materials, and basic unit operations, are not anticipated. The leading PTA (purified terephthalic acid) producers are expected to have greater optimization and energy integration across the entire production complex and more advanced control schemes. However, surpassing the current general expectation, this invention made a remarkable breakthrough to achieve improved catalyst activity and selectivity toward aromatic carboxylic acids, especially for PTA, in the aforementioned catalyst composition under milder oxidation conditions.

SUMMARY OF THE INVENTION

As a result of research for resolving the above problems, the inventors herein added one or more than one type of alkali metal or alkaline earth metal components (i.e., reagents or compounds comprising alkali metal or alkaline earth metal) to the catalyst of cobalt-manganese-bromine, in which a transition metal or lanthanide metal was also added as deemed necessary, during the manufacturing of aromatic carboxylic acids. The inventors also found that when an appropriate amount of carbon dioxide was added to the oxygen containing gas, which was supplied as an oxidant in the oxidation reaction, the reactivity not only dramatically increased, but the color properties of the product also increased along with reductions in the side reactions and the amount of impurities. Based on such findings, the present invention has been perfected.

In view of the foregoing, in one aspect, the present invention relates to a method of producing an aromatic carboxylic acid, the method comprising the steps of oxidizing, with a feed gas comprising oxygen and optionally carbon dioxide, an alkyl aromatic compound or a partially oxidized intermediate thereof, using a catalyst comprising (a) cobalt, manganese, and bromine, and (b) an alkali metal or alkaline earth metal dissolved in a solvent comprising an aliphatic carboxylic acid having 1 to 6 carbon atoms.

In another aspect, the present invention relates to a method of producing terephthalic acid by oxidizing para-xylene or para-toluic acid, the method comprising the steps of oxidizing, using a feed gas comprising oxygen and from 1% to 80% by volume of the feed gas of carbon dioxide, para-xylene or para-toluic acid, in the presence of a catalyst prepared by combining cobalt acetate tetrahydrate, manganese acetate tetrahydrate, hydrogen bromide, and potassium acetate.

In yet another aspect, the present invention relates to a method of producing phthalic acid or phthalic anhydride by oxidizing ortho-xylene, the method comprising the steps of oxidizing, using a feed gas comprising oxygen and from 1% to 80% by volume of the feed gas of carbon dioxide, ortho-xylene, in the presence of a catalyst prepared by combining cobalt acetate tetrahydrate, manganese acetate tetrahydrate, hydrogen bromide, and potassium acetate.

In a still further another aspect, the present invention relates to a process of purifying crude terephthalic acid products or crude isophthalic acid products containing partially-oxidized intermediates of alkyl aromatic compounds as impurities to obtain substantially pure terephthalic acid and isophthalic acid by using an above-discussed method.

In a still further aspect, the present invention relates to a method of producing an aromatic carboxylic acid, the method comprising the steps of oxidizing an alkyl aromatic compound or a partially oxidized intermediate thereof, with a gas (e.g., a feed gas or a reaction gas) comprising oxygen and at least 1% by volume of the gas of carbon dioxide, using a catalyst comprising (a) cobalt and manganese and (b) an alkali metal or alkaline earth metal.

In another aspect, the present invention relates to a method of producing terephthalic acid by oxidizing para-xylene or para-toluic acid, the method comprising the steps of oxidizing para-xylene or para-toluic acid, with a gas comprising oxygen and at least 1% by volume of the gas of carbon dioxide, in the presence of a catalyst prepared by combining cobalt acetate tetrahydrate, manganese acetate tetrahydrate, hydrogen bromide, and potassium acetate.

In yet another aspect, the present invention relates to a method of producing terephthalic acid by oxidizing para-xylene or para-toluic acid, the method comprising the steps of using carbon dioxide as a co-oxidant along with oxygen to oxidize para-xylene or para-toluic acid in the presence of a cobalt-manganese or nickel-manganese catalyst comprising an alkali metal or alkaline earth metal, thereby producing terephthalic acid, wherein the carbon dioxide is present in the gas phase in an amount of at least 1% by volume of the gas phase.

In still another aspect, the present invention relates to a method of producing phthalic acid or phthalic anhydride by oxidizing ortho-xylene, the method comprising the steps of oxidizing ortho-xylene, with a gas comprising oxygen and at least 1% by volume of the gas of carbon dioxide, in the presence of a catalyst prepared by combining cobalt acetate tetrahydrate, manganese acetate tetrahydrate, hydrogen bromide, and potassium acetate.

In a yet further aspect, the present invention relates to a method of producing an aromatic carboxylic acid, the method comprising the steps of oxidizing an alkyl aromatic compound or a partially oxidized intermediate thereof, with a gas comprising oxygen and an effective amount of carbon dioxide, the effective amount being an amount sufficient to exhibit action by the carbon dioxide as a co-oxidant, using a catalyst comprising (a) at least one transition metal and (b) an alkali metal or alkaline earth metal, thereby producing the aromatic carboxylic acid.

In another aspect, the present invention relates to a liquid phase $O_2$ oxidation of alkylaromatics such as p-, m-, and o-xylenes to the corresponding terephthalic acid, isophthalic acid, and phthalic anhydride with the MC-type catalyst, Co—Mn—Br, or a modified version of that catalyst further containing an alkali metal or alkaline earth metal, in the co-presence of $CO_2$, e.g.,

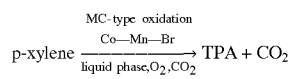

In another aspect, the present invention relates to a method of producing an aromatic carboxylic acid, the method comprising the steps of oxidizing an alkyl aromatic compound or a partially oxidized intermediate thereof, with a gas comprising oxygen with or without carbon dioxide, using a catalyst comprising (a) at least one transition metal and (b) an alkali metal or alkaline earth metal. Where the gas comprises oxygen and carbon dioxide, preferably the carbon dioxide is present in an effective amount (e.g., an amount greater than that present in air and sufficient to exhibit action by the carbon dioxide as a co-oxidant (e.g., as in the examples herein below)). More preferably the carbon dioxide is present in an amount of at least 1% by volume of the gas phase, and still more preferably at least 5% by volume of the gas phase. Other preferred ranges for carbon dioxide include at least 7%, at least 14%, and at least 28% by volume. The catalyst may comprise, e.g., (a) cobalt and manganese (which may be without, e.g., bromine or nickel) or (b) nickel and manganese. Further, where the catalyst comprises bromine, the mole ratio of the alkali or alkaline earth metal to bromine is preferably 0.001–5, more preferably 0.05–2, and most preferably 0.1–1.

In all of the foregoing aspects, the catalyst may comprise a conventional MC-type catalyst (e.g., a cobalt-manganese-bromine catalyst).

In yet another aspect, the present invention relates to a process of purifying crude terephthalic acid products or crude isophthalic acid products containing, as an impurity, a partially oxidized intermediate of an alkyl aromatic compound, to obtain substantially pure terephthalic acid or isophthalic acid by using an above-discussed method.

In a still further aspect, the present invention relates to a process comprising the steps of (a) obtaining the product of a liquid phase oxidation of an alkyl aromatic hydrocarbon using a cobalt-manganese-bromine catalyst, (b) thereafter, as a post-oxidation step, purifying the product obtained in the obtaining step to remove impurities therein using an above-discussed method.

In other aspects, the present invention relates to (a) an aromatic carboxylic acid prepared by an above-discussed method, (b) polyester made using the aromatic carboxylic acid, and (c) a product made using the polyester.

These and other aspects, objects, advantages, and features of the present invention will become apparent from the following detailed description of preferred embodiments thereof.

Unless otherwise stated, in this application, the concentration of gas is in volume %, the concentration of the catalyst is in weight ppm (by total weight of the reaction mixture), and the concentration of the product, and any other unspecified %, is in weight %.

Description of the Preferred Embodiments

The present invention relates to a production method of aromatic carboxylic acids, wherein alkylaromatic compounds or the oxidized intermediates thereof are oxidized by an oxygen containing gas, with an aliphatic carboxylic acid having 1–6 carbon atoms as a solvent, in the presence of a catalyst of cobalt-manganese-bromine with addition of a transition metal or lanthanide metal as deemed necessary. In the process, one or more than one type of alkali metal or alkaline earth metal components are added to the catalyst system with the process also featuring the addition of carbon dioxide to the oxygen containing gas, which is supplied as an oxidant.

Starting substances, i.e., alkylaromatic compounds or the oxidized intermediates thereof, to be oxidized in the present invention are preferably the compounds of benzene, naphthalene or similar aromatic compounds having one or more than one substituted alkyl groups (or a functional group having an oxidized alkyl group), such as para-xylene, para-tolualdehyde, para-toluic acid, 4-carboxybenzaldehyde, meta-xylene, meta-tolualdehyde, meta-toluic acid, 3-carboxybenzaldehyde, ortho-xylene, dimethylnaphthalene, pseudocumene (1,2,4-trimethylbenzene), mesitylene (1,3,5-trimethylbenzene), durene (1,2,4,5-tetramethylbenzene), 4,4'-dimethylbiphenyl, and toluene. More specifically, preferred alkyl aromatic compounds include para-xylene, meta-xylene, ortho-xylene, pseudocumene (1,2,4-trimethylbenzene), mesitylene (1,3,5-trimethylbenzene), durene (1,2,4,5-tetramethylbenzene), pentamethylbenzene, hexamethylbenzene, dimethylnaphthalene, 4,4'-dimethylbiphenyl, and toluene, while the partially oxidized alkyl aromatic intermediates preferably are para-toluic acid, meta-toluic acid, ortho-toluic acid, para-tolualdehyde, meta-tolualdehyde, ortho-tolualdehyde, 4-carboxybenzaldehyde, 3-carboxybenzaldehyde, or 2-carboxybenzaldehyde, and more preferably 4-carboxybenzaldehyde, 3-carboxybenzaldehyde, para-toluic acid, or meta-toluic acid.

The intended substances of the present invention, i.e., aromatic carboxylic acids, are preferably the compounds of benzene, naphthalene or similar aromatic compounds having one or more than one substituted carboxylic acid groups (or anhydrides with the removal of water by condensation of the carboxylic groups), such as terephthalic acid, isophthalic acid, phthalic acid, phthalic anhydrides, naphthalene dicarboxylic acid, trimellitic acid, trimellitic anhydrides, trimesic acid, pyromellitic dianhydride, 4,4'-biphenyldicaroboxylic acid, and benzoic acid, more preferably selected from the group consisting of terephthalic acid, phthalic acid, isophthalic acid, trimesic acid, trimellitic acid, trimellitic anhydride, and pyromellitic dianhydride, and most preferably terephthalic acid.

As for the basic catalyst in the present invention, a cobalt-manganese-bromine catalyst system was used. If deemed necessary, a transition metal or lanthanide metal component may be added. In the basic catalyst, the atomic weight ratio of manganese/cobalt is preferably 0.1~10, or more preferably 0.5~5. The atomic weight ratio of bromine/(manganese+cobalt) is preferably 0.1~10, or more preferably 0.5~2. The concentration of cobalt is preferably 20~10,000 ppm of the weight of the reactants (i.e., the substitute (the starting substance to be oxidized), the solvent, and the catalyst), or more preferably 50~1,000 ppm. As for the source of bromine, it could be a bromine compound, such as hydrogen bromide, potassium bromide, tetrabromoethane, etc. As for the source of manganese and cobalt, a compound which is soluble in solvents, such as acetate, carbonate, acetate tetrahydrate, bromide, etc. can be used, or more preferably, as a source of cobalt, manganese, bromine, respectively, are $Co(OAc)_2$ $H_2O$, $Mn(OAc)_2$ $4H_2O$, and hydrogen bromide.

Compounds of Ce, Zr, Hf, Mo, Cr, Fe, W, etc. are preferred for transition metals or lanthanide metals, which are added if necessary. The weight ratio of the added transition metal or lanthanide metal/manganese is appropriately 0.001~1. Further, the present invention can be applied to an oxidation reaction by a cobalt-manganese catalyst without bromine as well as a nickel-manganese-bromine catalyst.

The additive alkali metal or alkaline earth metal components used in the present invention can be any alkali metal or alkaline earth metal components. Specific examples include one or more than one type selected from Li, Na, K, Rb, Cs, Be, Mg, Ca, Sr or Ba, more preferably Na, K, and Cs, and most preferably K. These additive alkali metals or alkaline earth metals can be used in the forms of compounds having solubility in the solvents as used. Compounds such as acetate, acetate hydrate, bromide, chloride, fluoride, iodide, carbonate, carboxylate, alkoxide, azide, naphthenate, oxalate, acetylacetonate, hydroxide, nitrate, borate and oxide can be used. Among these, an acetate compound is most preferred. The mole ratio of the additive alkali metal or alkaline earth metal to bromine is appropriately 0.001~3, or more preferably 0.05~2, or most preferably 0.1~1. If the mole ratio is less than 0.001, the effect based on the addition of alkali metals or alkaline earth metals is not expected. If the mole ratio is more than 5, the retardation effect on the reaction is prevailing.

The solvent used in the present invention can be any aliphatic acids of $C_1$~$C_6$, such as formic acid, acetic acid, propionic acid, n-butyric acid, isobutyric acid, pentanoic acid, hexanoic acid, trimethylacetic acid, etc, or more preferably acetic acid or the mixture of acetic acid and water. Preferably, the solvent comprises from 2% to 25%, by weight, of water. The amount of solvent should be 1~10 times the weight of an alkylaromatic compound or the oxidized intermediate compound thereof. Further, the present invention can be applied to the oxidation reaction in water as a solvent.

As for the reaction gas used in the present invention, oxygen, or a gas mixture of oxygen and an inert gas such as nitrogen can be used, or more preferably, a gas mixture of oxygen and carbon dioxide can be used. Preferably, the reaction gas or feed gas lacks an inert diluent. The minimal pressure of the reaction is such that some portion of an alkylaromatic compound or the oxidized intermediate thereof and the solvent is maintained as liquid. The reaction pressure is appropriately 0~35 atm in terms of the gauge pressure or more preferably 8~30 atm.

The amount of carbon dioxide should be 1~80% (by volume) of the gas, or more preferably 5~50%. As for the method of adding carbon dioxide, it can be supplied in the gas phase at the upper part of the reactor or in the reactants of liquid phase, either periodically or continuously. (For example, carbon dioxide may be added with a gas sparging device into one or more zones of a reactor in a gas phase or liquid phase either periodically, intermittently, or in a continuous manner.) As for the method of supplying carbon dioxide to the reactor, carbon dioxide can be mixed into the reaction gas. Alternatively, the method of recycling the reacted vent gas to the reaction gas can be used for the purpose of utilizing carbon dioxide and oxygen remaining in the vent gas. (For example, carbon dioxide remaining in reaction vent gas may be recovered by condensation and recycled to provide carbon dioxide required for the oxidation reaction.) When it is supplied to the reactants in liquid, a dip tube etc. can be used for supplying via bubbling.

The production method of aromatic carboxylic acids of the present invention could be carried out by a batch type process or a continuous process. The appropriate reaction temperature should be 100~255° C., or more preferably 175~235° C., or most preferably 180~210° C. If the reaction temperature is too low, it is impractical since the reaction rate is too slow. If the reaction temperature is too high, it is non-economical due to the excessive side reactions.

As a reactor, general CSTR (continuous stirred tank reactor) or LOR (liquid oxygen reactor) specially designed to mix liquid oxygen and liquid hydrocarbon substrates without appreciable loss of unreached oxygen into the overhead vapor space can be used.

According to the present invention, the reaction time is decreased at the same reaction temperature for obtaining the same conversion. At the same reaction time, the present invention requires a lower reaction temperature for a given conversion. The productivity and quality such as chemical impurities and color properties can be improved due to the decreased side reactions with the present invention.

The present invention is explained in detail by examples below. Nevertheless, the examples are illustrative only and should not be deemed to limit the present invention.

EXAMPLES 1 THROUGH 6

(Production of terephthalic acid by the oxidation of para-xylene at the same oxygen consumption level—the oxidation reaction was terminated when the 85% of the theoretical amount of oxygen calculated based on the stoichiometry of the desired oxidation reaction was consumed; the results are shown in Table 1.)

Example 1

To a titanium pressure reactor, 200 g of reactants were added (i.e., water, para-xylene, acetic acid, and the catalyst). While stirring, the reaction temperature was raised to 185° C. in the atmosphere of nitrogen. The composition of the reactants (i.e., the reaction mixture) was adjusted to become 7.5% of water, 15% of para-xylene, and 77.5% of acetic acid. Based on the total weight of reactants, the catalyst was comprised of 100 ppm of cobalt, 200 ppm of manganese, and 300 ppm of bromine. Cobalt acetate tetrahydrate, manganese acetate tetrahydrate and hydrogen bromide were used (for the catalyst). As for the additive alkali metals or alkaline earth metals, potassium acetate was added to make the concentration of potassium in the total catalyst system to be 147 ppm. At the reaction temperature of 185° C., nitrogen was added up to 16.8 atm, and then oxygen was instantaneously added so that the concentration of oxygen in the gas phase became 40%. When the reaction pressure reached 28 atm, the amount of consumed oxygen was measured with time, and the oxygen was continuously fed to maintain at the same pressure (28 atm) to compensate the amount of oxygen consumed in the oxidation reaction. When the oxygen consumption reached 85% of the theoretical oxygen amount based on the stoichiometry of the desired oxidation reaction (reaction time: 63.2 minutes), the reactor was allowed to cool to terminate the reaction. The product obtained in this manner was subjected to a solid-liquid separation such as filtration. The solid was dried and analyzed along with the mother liquor, and the yield and purity of the product were calculated. The experimental conditions, the amount of oxygen consumed with reaction time, and the yield and purity of terephthalic acid product are compared with those of the Comparative Example 1 in Table 1. The yield of the terephthalic acid product was similar, but the purity of the product (80.3%) was higher for the run with 147 ppm potassium in Example 1 than that (78.2%) of the Comparative Example 1. The results also clearly showed that the reaction rate was increased in the presence of potassium, as shown in the run of Example 1, Table 1, and that side reactions such as burning were decreased in the same oxidation run.

Examples 2~4

The oxidation reactions of para-xylene were carried out in the identical manner to Example 1 except that the concentration of the added potassium was varied to be 15 ppm, 50 ppm, and 300 ppm in Examples 2, 3, and 4, respectively. It required a longer time, (72.2, 67.5, and 66.2 minutes, respectively) in these runs than that ( 63.2 minutes) for the run of Example 1 containing 147 ppm potassium to consume the 85% of the theoretical amount of oxygen based on the stoichiometry of the oxidation reaction. The experimental conditions, the amount of oxygen consumed with reaction time, and the yield and purity of the product are summarized in Table 1.

The yield of the terephthalic acid product was varied in the range of 58.6%~60.5% and the purity of the same product was slightly decreased from 82.4%, 77.9% and 77.5% as the concentration of potassium was varied from 15 ppm in Example 2, 50 ppm in Example 3, and to 300 ppm in Example 4, respectively.

However, the rate of the oxidation reaction was increased and side reactions such as burning were correspondingly decreased in all runs with potassium, Example 1–4, over the run without potassium, Comparative Example 1.

Examples 5 and 6

The oxidation reactions of para-xylene were carried out in the identical manner to Example 1, except that the concentrations of carbon dioxide in the feed gas was varied from 0% to 14% and 7%, respectively, in Examples 5 and 6. In other words, the gas phase was comprised of 46% of nitrogen, 14% of carbon dioxide and 40% of oxygen in Example 5, and 53% of nitrogen, 7% of carbon dioxide and 40% of oxygen in Example 6, respectively. The results are summarized in Table 1. It required 60.8 minutes for Example 5 and 62.0 minutes for Example 6 to consume the 85% of the theoretical amount of oxygen calculated based on the stoichiometry of the oxidation reaction. In other words, the rate of the oxidation reaction became faster when p-xylene was oxidized in the liquid phase with the catalyst system containing potassium by the co-presence of carbon dioxide mixed in the oxygen containing feed gas (see Examples 5–6 vs Examples 1–4, Table 1). The rate of the oxidation observed in Example 5 and 6 was further improved over the run in Comparative Example 1, which was oxidized with oxygen alone in the absence of carbon dioxide by the catalyst without potassium.

Comparative Example 1

The oxidation reaction of para-xylene was carried out in the identical manner to Example 1 except that potassium acetate was not added in the catalyst. It required 73.2 minutes to consume the 85% of the theoretical amount of oxygen based on the stoichiometry of the oxidation reaction. The results are compared in Table 1. The yield and purity of the product, terephthalic acid, in the Comparative Example 1 are similar to those in Example 1. But the reaction rate was slower in the comparative run, 73.2 minutes vs 63.2 minutes. The side reaction such as burning was increased in the run of the Comparative Example 1 judging from the results that both carbon monoxide and carbon dioxide in the spent gas were slightly increased from 5.8~6.4% to 6.4% and from 19.2~19.7% to 19.9%, respectively.

reactor with a lower ratio of height/width was used. The oxidation of para-xylene was run for 60 minutes under the conditions described in Table 2, 741.4 mmol of oxygen was consumed. The results compared with the catalyst system without potassium (Comparative Example 2) in Table 2 showed that the yield and the purity of the terephthalic acid product were significantly increased by adding potassium acetate in a level of 147 ppm on the basis of potassium.

Example 8

The oxidation reaction of para-xylene was carried out in the identical manner to Example 7, except that potassium carbonate was used instead of potassium acetate as a source of potassium. The oxidation reaction was conducted in the catalyst system containing 147 ppm potassium for a period of 60 minutes. The results summarized in Table 2 show that 725.3 mmol of oxygen was consumed, and that the yield and purity of the terephthalic acid product are somewhat lower than those in Example 7, but are much better than those of Comparative Example 2 without employing potassium acetate.

Examples 9 and 10

The oxidation reactions of para-xylene were carried out in the identical manner to Example 7, except that carbon dioxide was added to the oxygen containing feed gas stream so that the concentration of carbon dioxide in gas phase reached to the level of 14% and 7%, respectively. In other words, the gas phase was comprised of 46% of nitrogen, 14% of carbon dioxide and 40% of oxygen in Example 9, and 53% of nitrogen, 7% of carbon dioxide and 40% of oxygen in Example 10, respectively. The oxidation was conducted in the co-presence of carbon dioxide in the designated amount under the condition defined in Table 2 for a period of 60 minutes. In these runs, significantly higher

TABLE 1

Results of oxidation of para-xylene at the same oxygen consumption
(Reaction was terminated at 85% of the total oxygen consumption based on stoichiometry of the desired oxidation reaction)

| Exmp. | Additive Metal Component | Concentration of additive Metal Component (wt. ppm) | Concentration of Carbon Dioxide (vol. %) | Reaction Time (Minutes) * | Consumed Oxygen with Reaction Time (mmol)** | | | | TPA Yield (wt. %) | Purity of Solid (wt. %) | Concentration of $CO_2$ in gas phase after Reaction (vol. %) | Concentration of CO in gas phase after Reaction (vol. %) |
|---|---|---|---|---|---|---|---|---|---|---|---|---|
| | | | | | 15 Min | 30 Min | 45 Min | 60 Min | | | | |
| 1 | K | 147 | 0 | 63.2 | 235.0 | 417.8 | 582.4 | 691.6 | 58.3 | 80.3 | 19.7 | 6.0 |
| 2 | K | 15 | 0 | 72.2 | 240.0 | 408.7 | 545.2 | 647.7 | 58.6 | 82.4 | 19.5 | 5.8 |
| 3 | K | 50 | 0 | 67.5 | 240.1 | 411.0 | 559.2 | 669.9 | 60.5 | 77.9 | 19.2 | 6.2 |
| 4 | K | 300 | 0 | 66.2 | 205.9 | 385.9 | 546.2 | 670.1 | 59.2 | 77.5 | 19.7 | 6.4 |
| 5 | K | 147 | 14 | 60.8 | 245.8 | 435.2 | 598.9 | 713.8 | 57.6 | 78.6 | — | 6.3 |
| 6 | K | 147 | 7 | 62.0 | 238.0 | 419.4 | 588.4 | 707.1 | 59.5 | 83.1 | — | 6.2 |
| Comp. Exmp. 1 | — | — | 0 | 73.2 | 244.1 | 408.7 | 547.7 | 642.4 | 58.2 | 78.2 | 19.9 | 6.4 |

* Reaction time for 85% of the theoretical oxygen consumption by stoichiometry of the oxidation reaction,
** Theoretical oxygen consumption based on the stoichiometry of the oxidation reaction = 848 mmol.

EXAMPLES 7 THROUGH 21
(Oxidation of para-xylene for a fixed period of time (60 minutes); the results are shown in Table 2.)

Example 7

The oxidation reaction of para-xylene was carried out in the identical manner to Example 1, except that a pressure amounts of oxygen, i.e., 785.3 mmol and 768.8 mmol of oxygen, were consumed for Example 9 and 10, respectively, in comparison to 741.4 mmol for Example 7 and 725.3 mmol for Example 8 in which the oxidation was run with oxygen alone in the absence of carbon dioxide. These results clearly prove that the reaction rate improves remarkably by the co-presence of carbon dioxide in the catalyst system containing potassium.

Example 11

The oxidation reaction of para-xylene was carried out in the identical manner to Example 7, except that 26 ppm of lithium was added instead of potassium. The source of lithium was lithium nitrate. After 60 minutes of reaction, it was observed that 723.0 mmol of oxygen was consumed. The results listed in Table 2 indicate that lithium is less effective than potassium as an alkali additive, and that it is still better than that of Comparative Example 2.

Example 12

The oxidation reaction of para-xylene was carried out in the identical manner to Example 11, except that carbon dioxide was added so that the concentration of carbon dioxide in the feed gas reached 14%. In other words, the gas phase was comprised of 46% of nitrogen, 14% of carbon dioxide and 40% of oxygen. The oxidation was run under the conditions described in Table 2 for 60 minutes. It was found that more oxygen (730.1 mmol) was consumed than the run of Example 11 (723.0 mmol) during the same reaction period, and that both the yield and purity of the terephthalic acid product were noticeably improved by the co-presence of carbon dioxide.

Example 13

The oxidation reaction of para-xylene was carried out in the identical manner to Example 7, except that 86 ppm of sodium was added instead of potassium. The source of sodium was acetate trihydrate. The oxidation reaction was carried out under the conditions described in Table 2 for a period of 60 minutes. It was observed that 747.1 mmol of oxygen was consumed in this run. These results showed that the effect of sodium was comparable to that of potassium, although the yield of the terephthalic acid product obtained in this case containing 86 ppm sodium was found to be lower than the case containing a level of 147 ppm of potassium, 57.8%~59.2% vs 55.8%.

Examples 14 and 15

The oxidation reactions of para-xylene were carried out in the identical manner to Example 7, except that 150 ppm and 499 ppm of cesium, respectively, were added instead of potassium in Example 14 and 15. The source of cesium was cesium acetate. The oxidation was complete in 60 minutes. It was found that 698.7 mmol and 724.2 mmol of oxygen were consumed for Example 14 and 15, respectively. The results show that the rates of the oxidation were slightly lower than those in Example 7 and 8 using potassium, although they were definitely higher than that of Comparative Example 2, which did not contain potassium as an alkali additive in the catalyst system.

Examples 16 and 17

The oxidation reactions of para-xylene were carried out in an identical manner to Examples 14 and 15, respectively, except that carbon dioxide was added to the oxygen containing feed gas to reach the levels of 50% and 14%, respectively, for Examples 16 and 17. In other words, the gas phase comprised of 10% of nitrogen, 50% of carbon dioxide and 40% of oxygen in Example 16 and 46% of nitrogen, 14% of carbon dioxide and 40% of oxygen in Example 17, respectively. The oxidation was carried out under the conditions defined in Table 2 with the feed gas containing oxygen and carbon dioxide for a period of 60 minutes. The results shown in Table 2 clearly reveal that the amounts of oxygen consumed for the oxidation in the co-presence of carbon dioxide and oxygen are a lot more than those of the counterparts employing oxygen alone. The data also show that cesium is an effective additive for the reaction, but it appears that the effectiveness of cesium is somewhat less than that of potassium. The yield and purity of the terephthalic acid product are 60.5%~62.0% and 83.2%~85.4% respectively in the co-presence of carbon dioxide and oxygen, which are superior to the results, 54.6% and 78.4%, obtained from the corresponding system with oxygen alone (see Example 15).

Example 18

The oxidation reaction of para-xylene was carried out in the identical manner to Example 7, except that 74 ppm of potassium and 250 ppm of cesium were simultaneously added as an alkali additive. The sources of potassium and cesium were acetates. The oxidation was conducted under the conditions described in Table 2 for 60 minutes. During this reaction period, 738.0 mmol of oxygen was consumed for oxidation. Based on this results, one can conclude that a mixture of potassium and cesium is an effective additive.

Example 19

The oxidation reaction of para-xylene was carried out in the identical manner to Example 18, except that carbon dioxide was added so that its concentration in the feed gas became 28%. In other words, the gas phase was comprised of 32% of nitrogen, 28% of carbon dioxide and 40% of oxygen. The oxidation reaction was run in the co-presence of carbon dioxide and oxygen for a period of 60 minutes. The amounts of oxygen consumed were found to be 748.8 mmol for this example and 738.0 mmol for the counterpart system in the absence of carbon dioxide (Example 18). By using carbon dioxide along with oxygen in the presence of potassium and cesium, the yield (60.8%) and purity of the product (84.0%) were kept high.

Example 20

The oxidation reaction of para-xylene was carried out in the identical manner to Example 7, except that 91 ppm of magnesium was added instead of potassium. The source of magnesium was magnesium nitrate hexahydrate. The results obtained from the oxidation carried out for 60 minutes show that magnesium is also an effective alkaline earth additive. The amount of oxygen consumed during the 60 minute reaction period was measured to be 729.9 mmol, which was more than that (687.2 mmol) observed in the control run, Comparative Example 2.

Example 21

The oxidation reaction of para-xylene was carried out in the identical manner to Example 20, except that carbon dioxide was added so that its concentration in the feed gas reached 14%. In other words, the gas phase was comprised of 46% of nitrogen, 14% of carbon dioxide and 40% of oxygen. After 60 minutes of oxidation under the condition defined in Table 2, it was found that 742.7 mmol of oxygen was consumed, and it was better than those (687.2 mmol and 729.9 mmol) of Comparative Example 2 and Example 20, Table 2. The yield (60.2%) and purity (82.7%) of the terephthalic acid product obtained from this run in the co-presence of carbon dioxide along with oxygen were much higher than those, 45.6% (yield) and 67.9% (purity), observed in the control run, Comparative Example 2. It was clearly shown that the rate of reaction was improved along with the yield and quality of the terephthalic acid product by carrying out the oxidation of p-xylene in the co-presence of carbon dioxide with oxygen by adding magnesium as an alkaline earth additive to the Co—Mn—Br catalyst system.

Comparative Example 2

The oxidation of para-xylene was carried out in an identical manner to Example 7, except that there was no alkali or alkaline earth metal additive in the catalyst system. The oxidation of para-xylene was conducted for a fixed period of 60 minutes under the controlled conditions shown in Table 2. The amount of oxygen consumed during this period was measured to be 687.4 mmol. The yield and purity of the terephthalic acid product were 45.6% and 67.0%, respectively, and these results served as the basic control data for comparison.

Comparative Example 3

The oxidation of para-xylene was carried out in the identical manner to Example 7, except that 600 ppm of potassium was used as an alkali additive to replace 147 ppm of potassium. The oxidation run was made under the controlled conditions described in Table 2 for a period of 60 minutes. The amount of oxygen consumed during this period was found to be 598.4 mmol, which served as a control data for comparison. The results showed that the reaction was very slow (the amount of oxygen consumed: 598.4 mmol) and the purity of the product (55.1%) was quite low.

Comparative Example 4

The oxidation of para-xylene was carried out in the identical manner to Example 7, except that 60 ppm of nickel and 147 ppm of potassium were added to the Co—Mn—Br catalyst system in the acetic acid medium. Potassium acetate and nickel acetate tetrahydrate were dissolved into the catalyst solution in order to study the effect of the alkali metal or alkaline earth metal component in the presence of nickel. The oxidation was run under the conditions listed in Table 2 for a period of 60 minutes. During the present reaction, 586.9 mmol of oxygen was consumed. This result led to conclude that the rate of oxidation was somewhat hampered by adding nickel (the amount of oxygen consume with potassium alone was 741.4 mmol for the same 60 minute period, see Example 7, Table 2).

TABLE 2

Results of para-xylene oxidation for the same reaction time.
(reaction time: 60 minutes)

| | Additive Metal Component | Additive Metal Source | Concentration of Additive Metals (wt. ppm) | Concentration of Carbon Dioxide (vol. %) | Amount of Consumed Oxygen (mmol) * | TPA Yield (wt. %) | Purity of Solid TPA wt. % | TPA (wt. %) in the Products |
|---|---|---|---|---|---|---|---|---|
| Example 7 | K | KOAc | 147 | 0 | 741.4 | 59.2 | 82.8 | 64.5 |
| Example 8 | K | $K_2CO_3$ | 147 | 0 | 725.3 | 57.8 | 78.4 | 61.1 |
| Example 9 | K | KOAc | 147 | 14 | 785.3 | 62.8 | 86.9 | 69.1 |
| Example 10 | K | KOAc | 147 | 7 | 768.8 | 62.2 | 86.1 | 68.1 |
| Example 11 | Li | $LiNO_3$ | 26 | 0 | 723.0 | 56.5 | 77.8 | 59.1 |
| Example 12 | Li | $LiNO_3$ | 26 | 14 | 730.1 | 59.9 | 80.3 | 63.2 |
| Example 13 | Na | NaOAc $3H_2O$ | 86 | 0 | 747.1 | 55.8 | 86.3 | 63.1 |
| Example 14 | Cs | CsOAc | 150 | 0 | 698.7 | — | — | — |
| Example 15 | Cs | CsOAc | 499 | 0 | 724.2 | 54.6 | 78.4 | 57.3 |
| Example 16 | Cs | CsOAc | 150 | 50 | 744.0 | 60.5 | 83.2 | 65.2 |
| Example 17 | Cs | CsOAc | 499 | 14 | 758.0 | 62.0 | 85.4 | 66.8 |
| Example 18 | K, Cs | KOAc, CsOAc | 74, 250 | 0 | 738.0 | — | — | — |
| Example 19 | K, Cs | KOAc, CsOAc | 74, 50 | 28 | 748.8 | 60.8 | 84.0 | 65.9 |
| Example 20 | Mg | $Mg(NO_3)_2$ $6H_2O$ | 91 | 0 | 729.9 | — | — | — |
| Example 21 | Mg | $Mg(NO_3)_2$ $6H_2O$ | 91 | 14 | 742.7 | 60.2 | 82.7 | 65.0 |
| Comp. Exp. 2 | — | — | — | 0 | 687.2 | 45.6 | 67.9 | 49.5 |
| Comp. Exp. 3 | K | KOAc | 600 | 0 | 598.4 | 33.5 | 55.1 | 36.5 |
| Comp. Exp. 4 | K, Ni | KOAc, $Ni(OAc)_2$ $.4H_2O$ | 147, 60 | 0 | 586.9 | — | — | — |

* Total oxygen consumption by stoichiometry of the oxidation reaction = 848 mmol

EXAMPLES 22 AND 23

(Oxidation of para-xylene for the fixed period of time (50 minutes) in the catalyst system containing additional transition metals; the results are shown in Table 3.)

Example 22

The oxidation of para-xylene was conducted in the identical manner to Example 7, except that 30 ppm of zirconium was added to the catalyst. The concentration of potassium was adjusted to become 98 ppm instead of 147 ppm. During the reaction of 50 minutes, 762.8 mmol of oxygen was consumed. When this result was compared with that (737.7 mmol) of Comparative Example 5, Table 3, it is obvious that the present catalyst system is more active.

Example 23

The oxidation reaction of para-xylene was carried out in the identical manner to Example 22, except that carbon dioxide was added in the oxygen containing feed gas at a level of 14%. In other words, the gas phase was comprised of 46% of nitrogen, 14% of carbon dioxide and 40% of oxygen. The oxidation was run under the conditions shown in Table 3 for a period of 50 minutes. It was found that 779.6 mmol of oxygen was consumed during this period. By adding carbon dioxide along with potassium and zirconium to the Co—Mn—Br catalyst system, the catalytic activity was further enhanced, 762.8 mmol for potassium alone and 737.7 mmol for the controlled run, Comparative Example 5, Table 3.

Comparative Example 5

The oxidation reaction was carried out in an identical manner to Example 22, except that the reaction was carried out without additive alkali or alkaline earth metals. In short, the oxidation of para-xylene was run in the absence of both carbon dioxide and an alkali additive for a period of 50 minutes. The amount of oxygen consumed in this control run was found to be 737.7 mmol, which was lower than those of Example 22 and 23 and could serve as a basis for comparison purposes.

alkali metal or alkaline earth metal components, the amount of sodium hydroxide was adjusted so that the concentration of Na became 30 ppm. After reaching a steady state, the reaction was carried out for 8 hours. Table 4 shows the compositions of the solid which was obtained after cooling and solid-liquid separation. In comparison with the case without sodium (Comparative Example 6), it showed that the concentration of the terephthalic acid product was increased in the products, and that of para-toluic acid was decreased. Further, the analytic results of oxygen, carbon dioxide and carbon monoxide in the vent gas are shown in Table 4. The oxygen concentration in vent gas decreased, and this means that the catalytic activity increased with the addition of an alkali additive metal, sodium. Judging from the results on the same level of oxygen consumption, it is clear that the side reactions are also suppressed at least attributing to a decrease in the production rates of carbon dioxide and carbon monoxide (refer to the $CO_x/O_2$ conversion).

Examples 25~27

The oxidation of para-xylene was carried out in the identical manner to Example 24, except that the additive metals and its concentrations were varied as described in Table 4, respectively. The results of these runs are summarized in Table 4 and are compared with the case without additive metals (Comparative Example 6, Table 4). It showed that the amounts of terephthalic acid contained in the products increased while those of para-toluic acid were decreased. The concentrations of oxygen remained in the vent gas were decreased, revealing that the catalytic activity increased with an alkali additive metal, sodium or potassium. The content of terephthalic acid contained in the solid

TABLE 3

Results of para-xylene oxidation with the catalyst systems containing an additional transition metal (30 ppm Zr) (fixed reaction period: 50 minutes)

| | Additive Metal Components | Additive Metal Source | Concentration of Additive Metals (wt. ppm) | Concentration of Carbon Dioxide (vol. %) | Amount of Consumed Oxygen (mmol)* |
|---|---|---|---|---|---|
| Example 22 | K, Zr | KOAc | 98, 30 | 0 | 762.8 |
| Example 23 | K, Zr | KOAc | 98, 30 | 14 | 779.6 |
| Comp. Exp. 5 | Zr | | 30 | 0 | 737.7 |

*Total oxygen consumption by stoichiometry of the oxidation reaction = 848 mmol

EXAMPLES 24 THROUGH 27
(Oxidation of para-xylene in a continuous reactor (low conversion); the results are summarized in Table 4.)

Example 24

To a 10 liter capacity titanium pressure reactor, the reactants and oxidation feed gas, air, were introduced to carry out an oxidation reaction in a continuous manner. The composition of the reactants was 4% of water, 15% of para-xylene and 81% of acetic acid. The catalyst was comprised of, on the basis of the total weight of the reactants, 100 ppm of cobalt, 200 ppm of manganese and 300 ppm of bromine. Cobalt acetate tetrahydrate, manganese acetate tetrahydrate, and hydrogen bromide were used. The reaction temperature was 185° C., and the residence time in the reactor was 61 minutes. Air was supplied therein so that the flow rate of air corresponded to the amount that the mole ratio of oxygen to para-xylene was 3.0. As for the additive products increased as the additive concentration increased from 50 ppm to 100 ppm (see Example 26 and 27), whereas the amount of both para-toluic acid and 4-CBA included in the product were correspondingly declined. This trend becomes much more conspicuous if the results of these runs are compared with that of Comparative Example 6.

Comparative Example 6

The oxidation reaction of para-xylene was carried out in the identical manner to Example 24, except that the reaction was conducted without additive metals. Judging from the amount of oxygen remained in the vent gas stream and the composition of the harvested solid product, it is safe to conclude that the catalytic activity is low. The contents of terephthalic acid and p-toluic acid in the solid product obtained in this control run were 44.3% (against 54.5~59.3% for Examples 24–27, Table 4) and 51.3% (against 36.3%~40.8% for Examples 27–24, Table 4), respectively.

TABLE 4

Results of oxidation of para-xylene in the continuous reactor (at low conversion)

| | Additive Metals and Concentration (wt. ppm) | Concentration of Solid Products (wt. %) | | P-toluic Acid | Concentration of Vent Gas (vol. %) | | | $CO_x/O_2$ Conversion |
|---|---|---|---|---|---|---|---|---|
| | | TPA | 4-CBA | | $O_2$ | CO | $CO_2$ | |
| Example 24 | Na, 30 | 54.5 | 4.7 | 40.8 | 7.68 | 0.33 | 1.04 | 1.89 |
| Example 25 | Na, 60 | 57.1 | 4.6 | 38.2 | 7.46 | 0.32 | 1.07 | 1.92 |
| Example 26 | K, 50 | 57.5 | 4.5 | 38.2 | 7.56 | 0.31 | 1.01 | 1.82 |
| Example 27 | K, 100 | 59.3 | 4.4 | 36.3 | 7.32 | 0.28 | 1.01 | 1.77 |
| Comp. Exp. 6 | — | 44.3 | 4.4 | 51.3 | 8.96 | 0.29 | 1.01 | 2.02 |

EXAMPLE 28

(Oxidation reaction of para-xylene in a continuous reactor (high conversion); the results are shown in Table 5.)

TABLE 5

Results of oxidation of para-xylene in the continuous reactor (at high conversion)

| | Additive Metals and Concentrations (wt. ppm) | Properties of Solid Products | | | Component of Waste Gas Oxygen (vol. %) |
|---|---|---|---|---|---|
| | | 4-CBA (wt. %) | b-value | Optical Density (at 340 nm) | |
| Example 28 | K, 70 | 0.52 | 4.3 | 0.8 | 5.7 |
| Comp. Exp. 7 | — | 0.57 | 4.8 | 1.0 | 5.7 |

Example 28

The oxidation of para-xylene was conducted in the similar manner to Example 24, except that the composition of the reactants was changed to 4% of water, 20% of para-xylene and 76% of acetic acid. Based on the total weight of the reactants, the concentrations of cobalt, manganese and bromide were respectively kept at the levels of 160 ppm, 320 ppm and 480 ppm. The reaction temperature was maintained at 195° C. and the flow rate of air was adjusted so that the mole ratio of oxygen to the para-xylene substrate became 3.9. As for the additive alkali metal or alkaline earth metal components, potassium hydroxide was added so that the concentration of potassium was 70 ppm. As compared with the case without an alkali metal additive (Comparative Example 7, Table 5), it is obvious that the level of the impurity in the solid products becomes lower while the color properties of the products were improved. It was observed that the concentration of oxygen in the vent gas remained the same (5.7%). However, the 4-CBA level in the product was lowered from 0.57% to 0.52%, and the b-value and the optical density at 340 nm were also improved from 4.8 to 4.3 and from 1.0 to 0.8, respectively. These results show that the catalytic selectivity and quality of the product, in particular the color property, are improved in Example 28 over those of Comparative Example 7.

Comparative Example 7

The oxidation reaction of para-xylene was carried out in the same manner as Example 28, except that the reaction was run in the absence of potassium additive. The results obtained from this run are summarized in Table 5, and provided the basis for comparison with those of Example 28.

EXAMPLES 29 AND 30

(Production of terephthalic acid by the oxidation of para-toluic acid; the oxidation reaction was carried out for a fixed length of time (40 minutes); the results are shown in Table 6.)

Example 29

The oxidation of para-toluic acid was carried out in the identical manner to Example 7, except that 19.23% of para-toluic acid was used instead of para-xylene, and acetic acid was 73.77%. The reaction was allowed to run for a period of 40 minutes, and the amount of oxygen consumed in the run was found to be 405.7 mmol. When this result was compared with that of Comparative Example 8, Table 6, it was obvious that the catalytic activity was enhanced in this example.

Example 30

The oxidation reaction of para-toluic acid was carried out in the identical manner to Example 29, except that carbon dioxide (14%) was added to the oxygen containing feed gas. In other words, the gas phase was comprised of 46% of nitrogen, 14% of carbon dioxide and 40% of oxygen. The oxidation was run for 40 minutes under the conditions shown in Table 6, and results are compared with those of Example 29 and Comparative Example 8 in Table 6. The amount of oxygen consumed during this oxidation was 415.2 mmol against 405.7 mmol observed in Example 29 and 391.1 mmol for Comparative Example 8. The results clearly showed that the oxidation rate of para-toluic acid was remarkably improved by adding carbon dioxide along with potassium, and that it was more significantly improved over the run in the absence of potassium and carbon dioxide, Comparative Example 8.

Comparative Example 8

The oxidation reaction of para-toluic acid was carried out in the same manner as Example 29, except that the reaction was carried out without additive metals. In short, the run was made with oxygen only in the catalyst system without potassium. The amount of oxygen consumed under the conditions described in Table 6 was measured to be 391.1 mmol. This value would serve as a basic control value for the comparison with those obtained from Example 29 and 30 in order to exhibit the beneficial effect of an alkali metal additive as well the co-presence of carbon dioxide in the oxygen containing feed gas stream.

Example 32

The oxidation reaction of ortho-xylene was continued in the identical manner to Example 31, except that the addition of carbon dioxide was adjusted so that the concentration of carbon dioxide in the oxygen containing feed gas stream became 14%. In other words, the gas phase comprised of 46% of nitrogen, 14% of carbon dioxide and 40% of oxygen. It was found that 589.3 mmol of oxygen was consumed during a time period of 60 minutes in the present run. This value is significantly better than those (552.8 mmol and 533.1 mmol, respectively) obtained from both Example 31 and Comparative Example 9.

TABLE 6

The oxidation of para-toluic acid (Reaction time : 40 minutes)

|  | Additive Metal Components | Additive Metal Source | Concentration of Additive Metals (wt. ppm) | Concentration of Carbon Dioxide (vol. %) | Amount of Consumed Oxygen (mmol)* |
|---|---|---|---|---|---|
| Example 29 | K | KOAc | 147 | 0 | 405.7 |
| Example 30 | K | KOAc | 147 | 14 | 415.2 |
| Comp. Exp. 8 | — | — | — | — | 391.1 |

*Total oxygen consumption by stoichiometry of the oxidation reaction = 424 mmol

EXAMPLES 31 AND 32

(The oxidation of ortho-xylene was conducted for a fixed length of time (60 minutes); the results are summarized in Table 7.)

Example 31

The oxidation reaction of ortho-xylene was carried out in the identical manner to Example 7, except that the amount of potassium was changed to 98 ppm, and ortho-xylene was employed as the substrate instead of para-xylene. The oxidation reaction was run by maintaining the temperature at 190° C. for a period of 60 minutes. The amounts of oxygen consumed at 20, 40 and 60 minutes of the reaction time intervals were tracked, and the results are listed in Table 7. In this run, 552.8 mmol of oxygen was consumed in 60 minutes. It is safe to conclude that the catalytic activity is increased in the present run over that (533.1 mmol) of Comparative Example 9.

Comparative Example 9

The oxidation of ortho-xylene was carried out in the identical manner to Example 31, except that the reaction was run with oxygen only in the absence of a metal additive in the catalyst system. It was found that 533.1 mmol of oxygen was consumed during a reaction period of 60 minutes. This serves as a control number for the comparison with the results from Example 31 and 32, in order to bring out the beneficial functions of an alkali metal additive and/or co-presence of carbon dioxide in the oxygen containing feed gas stream.

TABLE 7

Results of oxidation of ortho-xylene (reaction time : 60 minutes)

|  | Additive Metal Components | Source of Additive Metals | Concentration of Additive Metals (wt. ppm) | Concentration of Carbon Dioxide in Gas Phase (vol. %) | Amount of Consumed Oxygen (mmol)* | | |
|---|---|---|---|---|---|---|---|
|  |  |  |  |  | 20 Min | 40 Min | 60 Min |
| Example 31 | K | KOAc | 98 | 0 | 375.6 | 499.5 | 552.8 |
| Example 32 | K | KOAc | 98 | 14 | 390.5 | 526.6 | 589.3 |
| Comp. Exp. 9 | — | — | — | — | 368.6 | 488.1 | 533.1 |

*Total oxygen consumption by stoichiometry of the oxidation reaction = 848 mmol

In summary, the present invention discloses an improved process for the production of aromatic carboxylic acids, wherein alkyl aromatic compounds or partially oxidized intermediates thereof are oxidized with a catalyst system, Co—Mn—Br with one or more than one type of alkali metal and/or alkaline earth metal additive, in an acetic acid medium, with an oxygen feed gas containing a substantial amount of carbon dioxide.

The oxidation reaction of alkylaromatic substrates proceed more selectively with a much faster rate to produce aromatic carboxylic acids products of improved quality, than the conventional MC-type oxidation process. The oxidation reaction occurs under conditions milder than that of the conventional process, and produced aromatic carboxylic acid products of higher purity (containing less impurities such as partially oxidized intermediate oxygenates and high molecular weight byproducts etc.) and better color property (improved b-value and optical density at 340 nm) in higher yield. In other words, the yield and quality of the aromatic carboxylic acid product such as terephthalic acid were improved significantly beyond the current general expectations of the world-wide PTA producers by conducting the oxidation reaction in a catalyst system containing an alkali metal and/or alkaline earth metal additive in addition to Co—Mn—Br with the mixed feed gas containing oxygen with or without a substantial amount of carbon dioxide in an acetic acid medium under relatively mild conditions. Another catalyst system, in which the cobalt-manganese-bromine system containing an additional transition metal or lanthanide series metal in addition to potassium, is also revealed in the present invention.

Furthermore, the oxidation reaction of the present invention may be used for purifying the products of a conventional MC-type process. For example, after obtaining the product of a conventional MC-type process (e.g., the product of a liquid phase oxidation of an alkyl aromatic hydrocarbon using a cobalt-manganese-bromine catalyst), thereafter, as a post-oxidation step, the oxidation reaction of the present invention can be applied to purify the product to remove impurities. More specifically, for example, the oxidation reaction of the present invention can be applied to purify crude terephthalic acid products or crude isophthalic acid products containing partially-oxidized intermediate impurities to obtain substantially pure terephthalic acid and isophthalic acid. Furthermore, the aromatic carboxylic acids made by the oxidation reaction of the present invention can be used to make polyester, or other products.

In conclusion, this invention discovered for the first time that carbon dioxide functioned as a co-oxidant along with oxygen in the MC-type oxidation process of alkylaromatics such as para-xylene. This findings led to production of aromatic carboxylic acid such as terephthalic acid of higher yield and remarkably improved quality.

In particular, it was found that in the present invention (a) $CO_2$ is capable of modulating the oxidative property of $O_2$ over the Co—Mn—Br catalyst, (b) the oxidation rate was increased (i.e., enhanced catalytic activity), (c) the oxidation became more selective toward the desired product (i.e., increased selectivity), (d) the reaction product distribution was dramatically altered (i.e., purer production formation), (e) much lower amounts of the partially oxidized products were found in the final acid product (thus, the present invention can be used for a purification process of crude terephthalic acid and isophthalic acid), (f) under identical reaction conditions (as compared to the conventional MC-type process), the reaction temperature required to obtain the same level of the conversion (activity) becomes much lower (in other words, the same product yield can be obtained at much lower temperatures, or the product yield can be much higher at the same temperature, and thus a much smaller reactor is required, resulting in an economically more attractive process), (g) a higher concentration of $O_2$ can be used in the reactor without causing an explosion or burning (i.e., safer operation is feasible), and (h) less burning occurs, promoting higher selectivity toward the desired main product, TPA. These findings are believed to be attributed to the generation of a very active oxygen species for the oxidation reaction (the oxygen species being more active than that provided by molecular dioxygen ($O_2$)) created from an intermediate complex of peroxocarbonate form in the co-presence of $CO_2$ and $O_2$ over an MC-type catalyst (cobalt-manganese-bromine), the peroxocarbonate being believed to be of the following form:

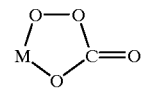

where M is Mn or Co.

The experimental results also indicate that the co-presence of alkali metal or alkaline earth metal further promotes the oxidation mechanism involving the above active species, peroxocarbonate.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method of producing an aromatic carboxylic acid, said method comprising the steps of:
   oxidizing, with a feed gas comprising oxygen and optionally carbon dioxide, an alkyl aromatic compound or a partially oxidized intermediate thereof, using a catalyst comprising (a) cobalt, manganese, and bromine, and (b) an alkali metal or alkaline earth metal dissolved in a solvent comprising an aliphatic carboxylic acid having 1 to 6 carbon atoms.

2. A method according to claim 1, wherein the catalyst further comprises a transition metal or lanthanide metal.

3. A method according to claim 2, wherein the transition metal or lanthanide metal is selected from the group consisting of zirconium, hafnium, cerium, iron, molybdenum, chromium, and tungsten.

4. A method according to claim 2, wherein the feed gas comprises carbon dioxide.

5. A method according to claim 4, wherein the concentration of carbon dioxide is 1% to 80%, by volume, of the feed gas.

6. A method according to claim 5, wherein the concentration of carbon dioxide is 5% to 50%, by volume, of the feed gas.

7. A method according to claim 6, wherein the feed gas lacks an inert diluent.

8. A method according to claim 1, wherein the feed gas comprises carbon dioxide.

9. A method according to claim 8, wherein the concentration of carbon dioxide is 1% to 80%, by volume, of the feed gas.

10. A method according to claim 9, wherein the concentration of carbon dioxide is 5% to 50%, by volume, of the feed gas.

11. A method according to claim 10, wherein the feed gas lacks an inert diluent.

12. A method according to any of claims 4 through 11, wherein the carbon dioxide is added with a gas sparging device into one or more zones of a reactor in a gas phase or liquid phase either periodically, intermittently, or in a continuous manner.

13. A method according to any of claims 4 through 11, wherein the carbon dioxide is mixed into the feed gas, or carbon dioxide remaining in reaction vent gas is recovered by condensation and is recycled to provide carbon dioxide required for the oxidation reaction.

14. A method according to claim 1, wherein the alkyl aromatic compound is selected from the group consisting of para-xylene, meta-xylene, ortho-xylene, pseudocumene (1,2,4-trimethylbenzene), mesitylene (1,3,5-trimethylbenzene), durene (1,2,4,5-tetramethylbenzene), pentamethylbenzene, hexamethylbenzene, dimethylnaphthalene, 4,4'-dimethylbiphenyl, and toluene.

15. A method according to claim 1, wherein the partially oxidized alkyl aromatic intermediate is selected from the group consisting of para-toluic acid, meta-toluic acid, ortho-toluic acid, para-tolualdehyde, meta-tolualdehyde, ortho-tolualdehyde, 4-carboxybenzaldehyde, 3-carboxybenzaldehyde, and 2-carboxybenzaldehyde.

16. A method according to claim 15, wherein the partially oxidized alkyl aromatic intermediate is selected from the group consisting of 4-carboxybenzaldehye, 3-carboxybenzaldehyde, para-toluic acid, and meta-toluic acid.

17. A method according to claim 1, wherein the aromatic carboxylic acid is selected from the group consisting of terephthalic acid, isophthalic acid, phthalic acid, phthalic anhydride, naphthalene dicarboxylic acid, trimellitic acid, trimellitic anhydride, trimesic acid, pyromellitic dianhydride, benzene pentacarboxylic acid, benzene hexacarboxylic acid, 4,4'-biphenyldicarboxylic acid, and benzoic acid.

18. A method according to claim 17, wherein the aromatic carboxylic acid is selected from the group consisting of terephthalic acid, phthalic acid, isophthalic acid, trimesic acid, trimellitic acid, trimellitic anhydride, and pyromellitic dianhydride.

19. A method according to claim 18, wherein the aromatic carboxylic acid is terephthalic acid.

20. A method according to claim 1, wherein the alkali metal or alkaline earth metal is selected from the group consisting of Li, Na, K, Rb, Cs, Be, Mg, Ca, Sr, and Ba.

21. A method according to claim 20, wherein the alkali metal or alkaline earth metal is selected from the group consisting of Na, K, and Cs.

22. A method according to claim 21, wherein the alkali metal or alkaline earth metal is K.

23. A method according to any of claims 1 and 20 through 22, wherein the alkali metal or alkaline earth metal is provided by a metal compound selected from the group consisting of acetate, acetate hydrate, bromide, chloride, fluoride, iodide, carbonate, carboxylate, alkoxide, azide, naphthenate, oxalate, octanoate, acetylacetonate, hydroxide, nitrate, borate, and oxide.

24. A method according to claim 1, wherein the mole ratio of alkali metal or alkaline earth metal to bromine is from 0.001 to 3.

25. A method according to claim 1, wherein the solvent comprises from 2% to 25%, by weight, of water.

26. A process of purifying crude terephthalic acid products or crude isophthalic acid products containing partially-oxidized intermediates of alkyl aromatic compounds as impurities to obtain substantially pure terephthalic acid and isophthalic acid by using the method according to claim 15.

27. A process according to claim 26, wherein the partially-oxidized intermediate impurities are selected from the group consisting of 4-carboxybenzaldehyde and 3-carboxybenzaldehyde.

28. A process comprising the steps of:
obtaining the product of a liquid phase oxidation of an alkyl aromatic hydrocarbon using a cobalt-manganese-bromine catalyst; and
thereafter, as a post-oxidation step, purifying the product obtained in said obtaining step to remove impurities therein using the method according to claim 1.

29. A method of producing terephthalic acid by oxidizing para-xylene or para-toluic acid, said method comprising the steps of:
oxidizing, using a feed gas comprising oxygen and from 5% to 50% by volume of the feed gas of carbon dioxide, para-xylene or para-toluic acid, in the presence of a catalyst prepared by combining cobalt acetate tetrahydrate, manganese acetate tetrahydrate, hydrogen bromide, and potassium acetate.

30. A method according to claim 29, wherein the only source of bromine in the catalyst used in said oxidizing step is one compound, the hydrogen bromide.

31. A method according to claim 29, wherein para-xylene is oxidized in said oxidizing step.

32. A method according to claim 29, wherein para-toluic acid is oxidized in said oxidizing step.

33. A method of producing phthalic acid or phthalic anhydride by oxidizing ortho-xylene, said method comprising the steps of:
oxidizing, using a feed gas comprising oxygen and from 5% to 50% by volume of the feed gas of carbon dioxide, ortho-xylene, in the presence of a catalyst prepared by combining cobalt acetate tetrahydrate, manganese acetate tetrahydrate, hydrogen bromide, and potassium acetate.

34. A method according to claim 2, wherein the transition metal or lanthanide metal is selected from the group consisting of zirconium, hafnium, and cerium.

35. A method according to claim 1, wherein the mole ratio of alkali metal or alkaline earth metal to bromine is from 0.05 to 2.

* * * * *

UNITED STATES PATENT AND TRADEMARK OFFICE
CERTIFICATE OF CORRECTION

PATENT NO. : 6,194,607 B1
DATED : February 27, 2001
INVENTOR(S) : Sung-Hwa Jhung et al.

It is certified that error appears in the above-identified patent and that said Letters Patent is hereby corrected as shown below:

Title page,
Item [56] References Cited, OTHER PUBLICATIONS, "Derivatives ," Allied" should read -- Derivatives," Applied --, "Dioxide" should read -- Dioxygen -- and "System" should read -- Systems --.

Column 4,
Line 54, "herein below" should read -- hereinbelow --.

Column 8,
Line 61, "Example 1-4" should read -- Examples 1-4 --.

Column 9,
Line 63, "20" should be deleted.

Column 12,
Line 31, "this" should read -- these --.

Column 14,
Line 24, "consume" should read -- consumed --.

Column 16,
Line 23, "its" should read -- their --.

Column 17,
Line 8, "1.92" should read -- 1.91 --.

Column 21,
Line 40, "findings" should read -- finding --.

UNITED STATES PATENT AND TRADEMARK OFFICE
CERTIFICATE OF CORRECTION

PATENT NO. : 6,194,607 B1
DATED : February 27, 2001
INVENTOR(S) : Sung-Hwa Jhung et al.

It is certified that error appears in the above-identified patent and that said Letters Patent is hereby corrected as shown below:

<u>Column 23,</u>
Line 21, "4-carboxybenzaldehye" should read -- 4-carboxybenzaldehyde --.

Signed and Sealed this

Seventh Day of May, 2002

*Attest:*

*Attesting Officer*

JAMES E. ROGAN
*Director of the United States Patent and Trademark Office*